(12) United States Patent
Fadler et al.

(10) Patent No.: US 10,863,954 B2
(45) Date of Patent: *Dec. 15, 2020

(54) APPARATUS FOR THE FLEXIBLE POSITIONING OF A RADIATION SOURCE AND A RADIATION DETECTOR

(71) Applicant: Siemens Healthcare GmbH, Erlangen (DE)

(72) Inventors: Franz Fadler, Hetzles (DE); Oliver Hornung, Fürth (DE)

(73) Assignee: Siemens Healthcare GmbH, Erlangen (DE)

( * ) Notice: Subject to any disclaimer, the term of this patent is extended or adjusted under 35 U.S.C. 154(b) by 415 days.

This patent is subject to a terminal disclaimer.

(21) Appl. No.: 15/175,028

(22) Filed: Jun. 6, 2016

(65) Prior Publication Data

US 2016/0287196 A1    Oct. 6, 2016

Related U.S. Application Data

(63) Continuation of application No. 12/877,649, filed on Sep. 8, 2010, now Pat. No. 10,595,802.

(30) Foreign Application Priority Data

Sep. 11, 2009    (DE) .................. 10 2009 041 172

(51) Int. Cl.
*A61B 6/00* (2006.01)

(52) U.S. Cl.
CPC .......... *A61B 6/4441* (2013.01); *A61B 6/4429* (2013.01); *A61B 6/4452* (2013.01);
(Continued)

(58) Field of Classification Search
CPC ... A61B 6/4429; A61B 6/4441; A61B 6/4452; A61B 6/4458; A61B 6/4464; A61B 6/56
See application file for complete search history.

(56) References Cited

U.S. PATENT DOCUMENTS 3,281,598 A    10/1966   Hollstein
4,426,725 A    1/1984    Grady
(Continued)

FOREIGN PATENT DOCUMENTS

CN    101378697 A    6/1999
CN    1220134 A      3/2009
(Continued)

OTHER PUBLICATIONS

Chinese office Action for related Chinese Application No. 201010282789.6 dated Dec. 27, 2013, with English Translation.
(Continued)

*Primary Examiner* — Christopher L Cook
(74) *Attorney, Agent, or Firm* — Lempia Summerfield Katz LLC

(57) ABSTRACT

An apparatus for medical examinations includes a first arm that is rotatable about an axis, the first arm being configured to carry a radiation source or a radiation detector. The apparatus for medical examinations also includes a second arm that is rotatable about the axis, the second arm being configured to carry a radiation source or a radiation detector. The second arm is attached to the first arm and is rotatable relative to the first arm.

16 Claims, 5 Drawing Sheets

(52) U.S. Cl.
CPC .......... *A61B 6/4458* (2013.01); *A61B 6/4464* (2013.01); *A61B 6/56* (2013.01)

(56) References Cited

U.S. PATENT DOCUMENTS

| | | | |
|---|---|---|---|
| 4,490,835 | A | 12/1984 | Wons |
| 4,979,196 | A * | 12/1990 | Lieutaud ............. A61B 6/502 378/195 |
| 5,055,821 | A | 10/1991 | Keller et al. |
| 5,523,571 | A | 6/1996 | Velazquez et al. |
| 6,104,780 | A | 8/2000 | Hanover et al. |
| 6,314,157 | B1 | 11/2001 | Tachizaki |
| 6,318,892 | B1 | 11/2001 | Suzuki et al. |
| 6,325,537 | B1 | 12/2001 | Watanabe |
| 6,373,060 | B1 * | 4/2002 | Yamakawa ......... G01T 1/1648 250/363.05 |
| 6,554,472 | B1 | 4/2003 | Dietz et al. |
| 6,637,936 | B2 | 10/2003 | Crain et al. |
| 7,885,379 | B2 | 2/2011 | Meer et al. |
| 2002/0118793 | A1 | 8/2002 | Horbaschek |
| 2007/0129846 | A1 | 6/2007 | Birkenbach et al. |
| 2008/0198973 | A1 | 8/2008 | Timmermans et al. |
| 2009/0118803 | A1 | 5/2009 | Fallik |
| 2009/0304159 | A1 | 12/2009 | Meer et al. |
| 2012/0267542 | A1 | 10/2012 | Wiener et al. |

FOREIGN PATENT DOCUMENTS

| | | |
|---|---|---|
| DE | 3138939 A1 | 4/1983 |
| DE | 3316719 A1 | 11/1983 |
| DE | 69823456 T2 | 5/2005 |
| DE | 102006005068 A1 | 8/2007 |
| DE | 102007021717 A1 | 10/2008 |
| EP | 0381785 A1 | 8/1990 |
| GB | 2084439 A | 4/1982 |
| JP | 06327662 A | 11/1994 |
| JP | 11099143 A | 4/1999 |
| JP | 2002263094 A | 9/2002 |
| JP | 2009072508 A | 4/2009 |
| WO | WO2007026282 A2 | 3/2007 |

OTHER PUBLICATIONS

Chinese office Action for related Chinese Application No. 201010282789.6 dated Jan. 15, 2015 with English Translation.
Chinese office Action for related Chinese Application No. 201010282789.6 dated Jul. 17, 2014, with English Translation.
German office Action for related German Application No. 10 2009 041 172.0 dated Aug. 21, 2014, with English Translation.
German office Action for related German Application No. 10 2009 041 172.0 dated Jul. 26, 2010, with English Translation.
Japanese Notice for Rejection for related Japanese Patent No. 2010-204678, dated Feb. 17, 2014 with English Translation.
German office Action for related German Application No. 10 2009 061 749.3 dated Sep. 5, 2016, with English Translation.

* cited by examiner

Slip-Ring between the Robot Hand and C-Arm

High Voltage Generator in/at the C-Arm

Systemic:
- Additional Load through Slip-Ring and High Voltage Generator
- Load Worn on TCP

APPARATUS FOR THE FLEXIBLE POSITIONING OF A RADIATION SOURCE AND A RADIATION DETECTOR

This application is a continuation of U.S. patent application Ser. No. 12/877,649, filed Sep. 8, 2010, which claims the benefit of DE 10 2009 041 172.0, filed Sep. 11, 2009. The entire contents of these documents are hereby incorporated herein by reference.

BACKGROUND

The present embodiments relate to an apparatus for medical examinations.

Medical imaging methods based on x-rays have a wide diagnostic application range. In current and future applications, several recordings are performed from different positions. This aims at a three-dimensional reconstruction of images, such as are realized, for example, in computed tomography, and image sequences are used for the complete diagnostic imaging of body regions to be examined. Angiography is an important field in which these aims prevail.

Angiography applications are gaining increased importance in terms of intraoperative imaging. In addition to the classical tasks of angiography modalities, such as angioplasty in the case of static but flexibly positionable imaging recording system, modern methods of 3D image reconstruction are gaining in importance. To generate this data, image sequences are recorded across accurately defined trajectories of the image recording system. These techniques can be implemented, to a certain extent, with the existing modalities (e.g., DynaCT, SpiralCT). The reconstruction quality is, however, not far from that of a 3D reconstruction with the aid of a modern CT device. Angiography examinations are, in many cases, currently implemented with C-arms, which are provided in part with hinged carrier systems for the description of trajectories. A C-arm system that is suitably for angiography is described, for example, in DE 10 2007 021 717 A1.

To increase the reconstruction quality, attempts have been made to increase the rotational speed of the C-arm and retain very high repetition accuracies for previously calibrated motion sequences. Since, in current devices, the axle bearings are restricted by the running of cables to the C-arm or by structural restrictions, a very high starting acceleration and, at the end of the movement, a very high braking acceleration of the rotation are realized in order to adhere to these aims. This is done to achieve a high final speed. From the drive technology or structural design point of view, which forms the basis for maintaining the repetition accuracy, these maximum accelerations are severely restricted. A way out of this conflict of aims would be to implement a continuous rotation, during which the projection sequence is only recorded when the C-arm is accelerated and rotates about the isocenter at a constantly high speed. By decoupling the acceleration process and the x-ray image recording, considerably improved reconstruction results are likely to be achieved for the previously cited reasons on the basis of very uniform movements. The implementation of such a continuous rotation is nevertheless problematic. A slip ring on a central rotational axis for the C-arm rotation may transmit numerous forms of energy and information. The high voltage (e.g., 75 kV) cannot be transmitted with current slip ring systems but is instead converted from approximately 3 kV using a high voltage transformer carried on the rotating side of the slip ring.

Improved concepts for the slip ring integration have been proposed, with, depending on the kinematic structure of the movement system, differently effective conditions being provided for the integration. Classical devices from the high-end range (e.g., some products from the Siemens Artis series) are very well qualified to implement an improved slip ring concept. FIG. 1 shows one design provided.

If highly flexible movements by the emitter and detector are desirable, the slip ring integration reaches its limits. As a result of the condition of a central decoupling axis for each continuous rotation, the slip ring is fastened to the last axis of a serial kinematic chain (A6). An additional load provided by the slip ring and high voltage transformer at the end point of the kinematic chain is therefore borne by the robot. This cannot, however, be realized technically with the appropriate precision. FIG. 2 identifies the potential installed location.

SUMMARY AND DESCRIPTION

The present embodiments may obviate one or more of the drawbacks or limitations in the related art. For example, an apparatus that is improved with respect to recording a sequence of images with different recording positions may be provided.

An apparatus for medical examinations includes a first arm that may be rotated about an axis, the first arm being configured to carry a radiation source or a radiation detector. The radiation source and/or detector may be attached in a region of an end of the first arm.

The apparatus for medical examinations also includes a second arm that may be rotated about the axis, at least in sections. The second arm is also configured to carry a radiation source or a detector (e.g., also in a region of an end of the second arm). In one embodiment, one of the arms (e.g., the first arm) carries the emitter and the other arm (e.g., the second arm) carries the detector. The second arm is attached and/or arranged on the first arm, so that the second arm rotates together with the rotation of the first arm. The second arm may also be rotated relative to the first arm.

The rigid C-arm is divided into two arms for the description of trajectories with respect to the region examined using the emitter and detector. The two arms may also include further degrees of freedom (e.g., using a telescopic spindle and/or rotary and pivot joints) in order to be able to better reproduce the trajectories. The second arm is attached to the first arm such that a rotation of the first arm also rotates the second arm. A relative maneuverability of the second arm relative to the first arm is also provided. With respect to the rotation of the arms, the movement is broken down into two different movement components (e.g., the rotation of the first arm, which is followed by the second arm, and a relative movement of the second arm. Rotations with high demands (e.g., full rotations) may be provided for an arm. By contrast, the second arm moves relatively little in many applications, since the rotation of the second arm is a relative movement with respect to the first arm. Full rotations of the second arm may not be needed; thus the apparatus may not be configured for full rotations of the second arm. It is also advantageous that implemented examinations may be realized with a rigid C-arm, where the second arm remains rigid and does not move relative to the first arm but instead rotates along with the first arm.

In one embodiment, a first end of the first arm is formed by a solid body. The first end of the first arm may become the end of the axis of rotation. A solid body may be a body that affords space for and/or is configured for accepting at least one component that is used for the functions of the apparatus. The second arm is attached to the solid body. The solid body may be configured in a rotationally symmetrical fashion relative to the axis. Drives for the first and the second arm may be provided. The drive for the second arm may be arranged in the solid body. In one embodiment, an energy or data transmission may be performed using a slip ring. The first arm may be rotatably fastened to a stand that is configured as a ceiling or floor stand, for example.

DETAILED DESCRIPTION OF THE DRAWINGS

Figure 1:
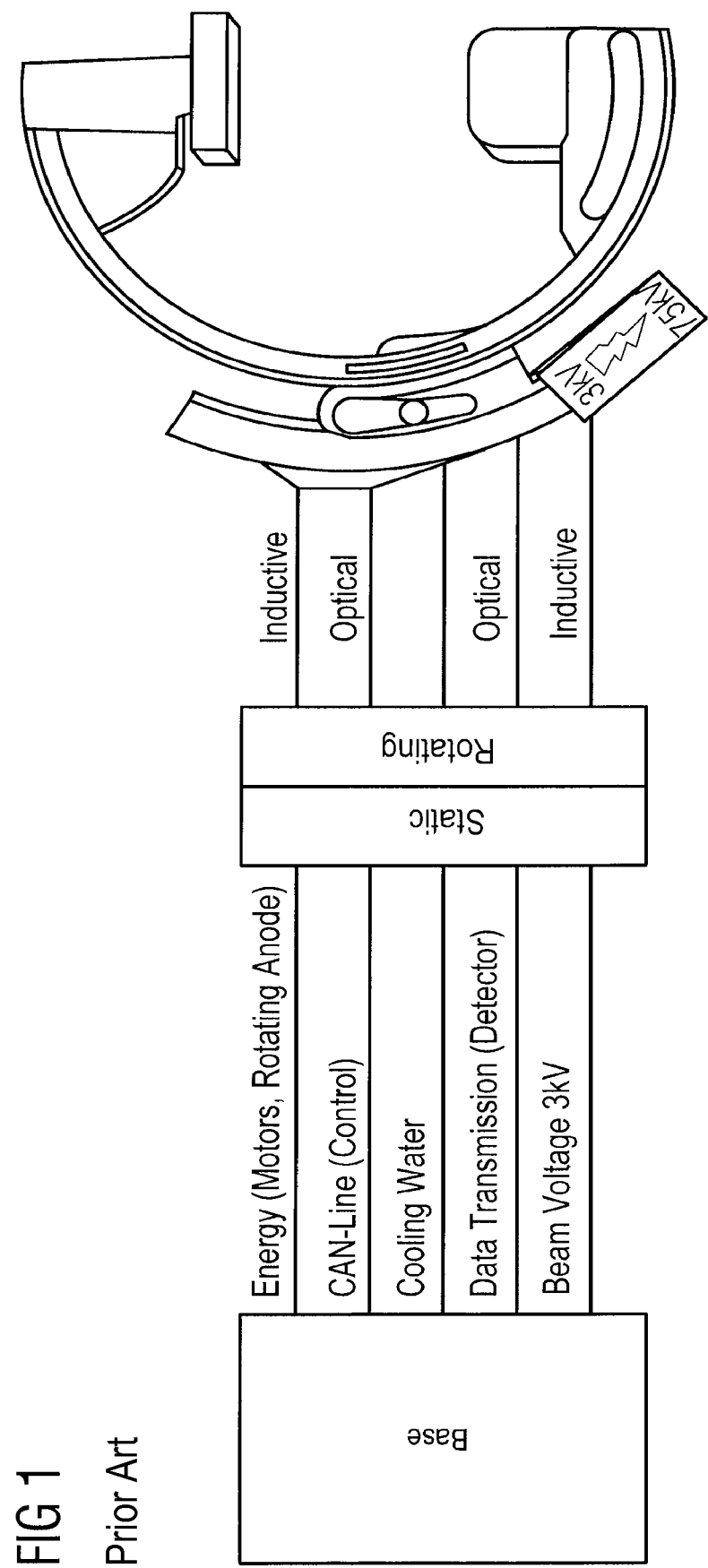
FIG. 1 shows a schematic representation of a conventional C-arm.

FIG. 1 shows a schematic representation of a conventional rotating C-arm. The C-arm includes a non-rotating base and a rotating arc. The non-rotating and/or static base includes a plurality of elements that are used for the operation of the C-arm. For example, the non-rotating base includes components for energy supply (e.g., motors, rotary anode), control line (e.g., CAN-BUS), cooling water supply, data transmission components (e.g., for data received by the detector) and components for generating an emitter voltage of 3 KV, for example. The rotating part and/or arc includes apparatus elements for the transmission of energy and data (e.g., transmission may be optical, inductive or capacitive) and components for transforming the voltage to a high voltage (e.g., 3 KV to 75 KV).

Figure 2:
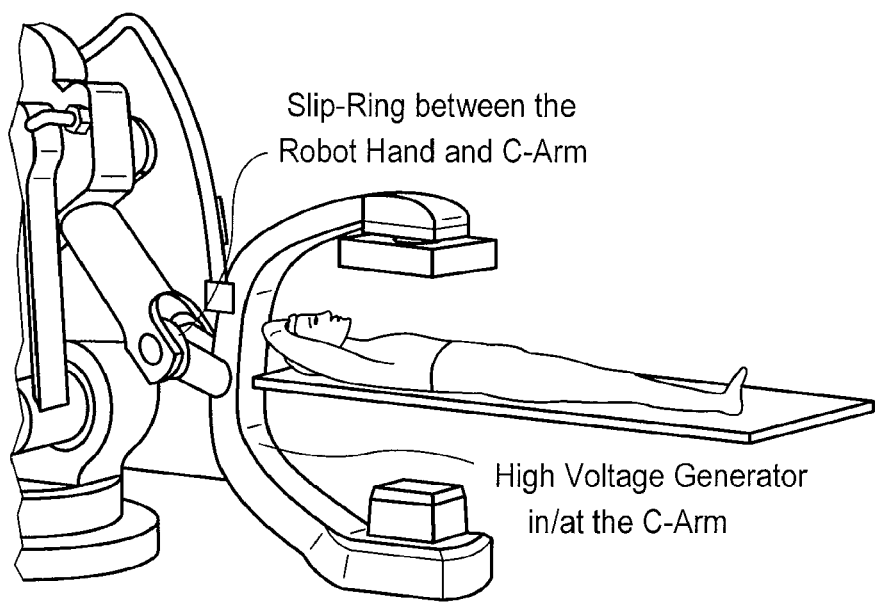
FIG. 2 shows a conventional C-arm.

FIG. 2 shows a conventional C-arm with a slip ring provided between the robot hand and the C-arm for the supply of data and energy to a high voltage generator in or on the C-arm. This C-arm has limits if a rigid C-arm is forgone in favor of a more flexible C-arm.

Figure 3:
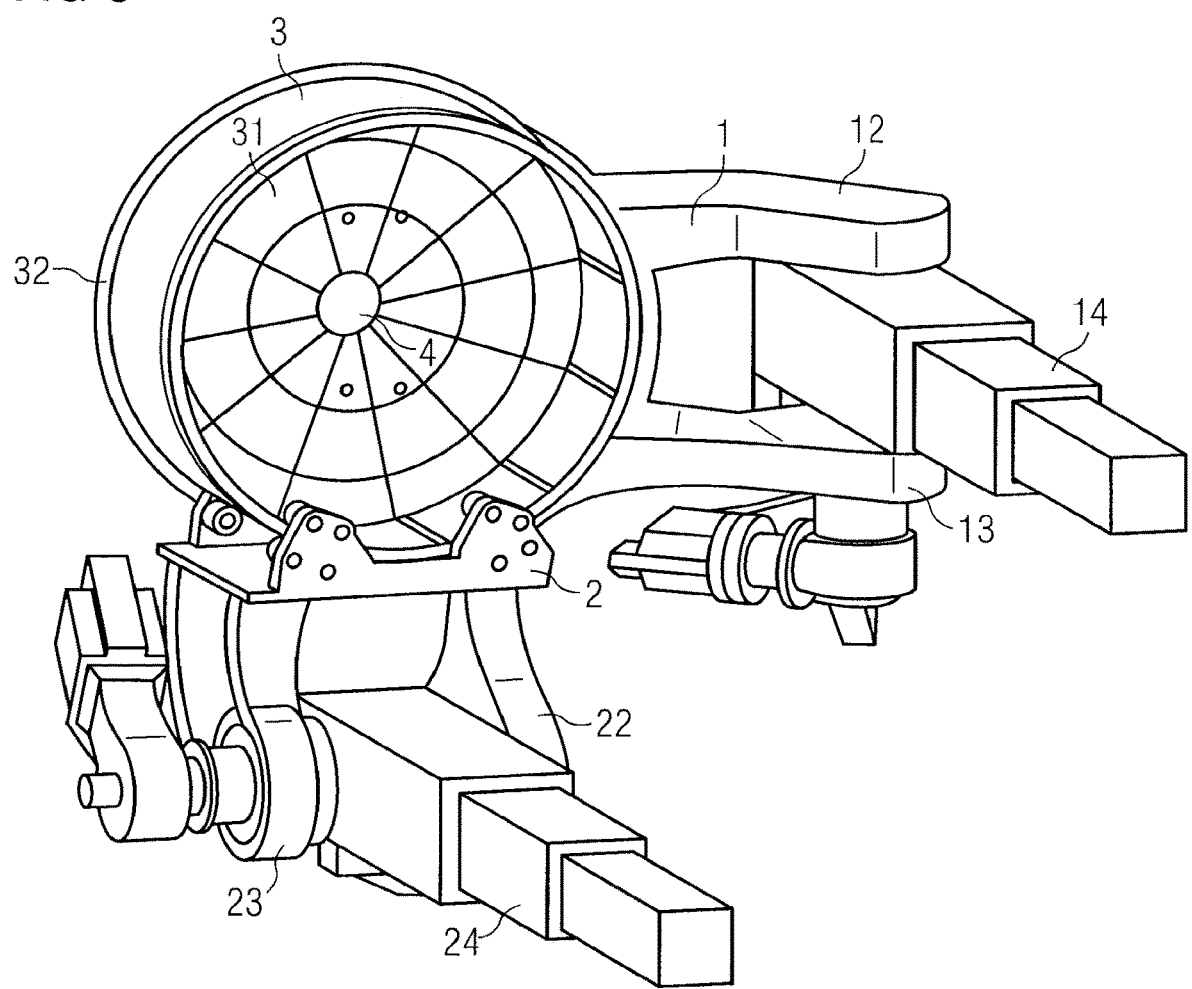
FIG. 3 shows the attachment of arms of one embodiment of an apparatus for medical examinations.

FIG. 3 shows the attachment of arms of one embodiment of an apparatus for medical examinations. The apparatus for medical examinations includes a first arm 1 and a second arm 2. An end of the first arm 1 is formed by a solid body 3. The second arm 2 is rotatably fastened to this solid body 3. The second arm 2 rotates relative to the first arm 1 (e.g., the second arm 2 performs the movements of the first arm 1, which are superimposed by the relative movements and/or the relative rotation of the second arm 2). The first arm 1 may be a master or master arm, and the second arm 2 may be a slave or a slave arm. The first arm 1 includes a section 12 that adjoins the solid body 3, a hinge 13 and an arm section 14; the arm section 14 is connected to the section 12 with the hinge 13. The second arm 2 includes a section 22 that adjoins the solid body 3, a hinge 23 and an arm section 24; the arm section 24 is connected to the section 22 with the hinge 23. The arm section 14 and/or the arm section 24 may be configured like a telescope. The solid body 3 includes a rear wall 31 and a side wall 32. The first arm 1 and the second arm 2 are fastened to the side wall 32, with the second arm 2 being rotatable along the side wall 32, so that the relative position of the first arm 1 and the second arm 2 may be changed by rotation about the solid body 3. In the embodiment shown in FIG. 3, the first arm 1 and the second arm 2 make an angle of 90°. A round recess 4 is shown in the rear wall 31 of the solid body 3. The recess 4 corresponds to an axis about which the two arms 1 and 2 rotate.

The present embodiments allow for the use of conventional slip rings (e.g., for the transmission of data/energy between a static part and the first arm 1 or between the first arm 1 and the second arm 2). The solid body 3 is suited to receiving system components (e.g., high voltage, drive controller, power electronics). If no relative movement is needed (e.g., with conventional C-arm inserts), this treatment situation may be realized by the second arm 2 not being rotated relative to the first arm 1 (e.g., by only one drive such as a drive of the arm 1 rotating both arms 1 and 2 in a fixed positioning relative to one another).

Figure 4:
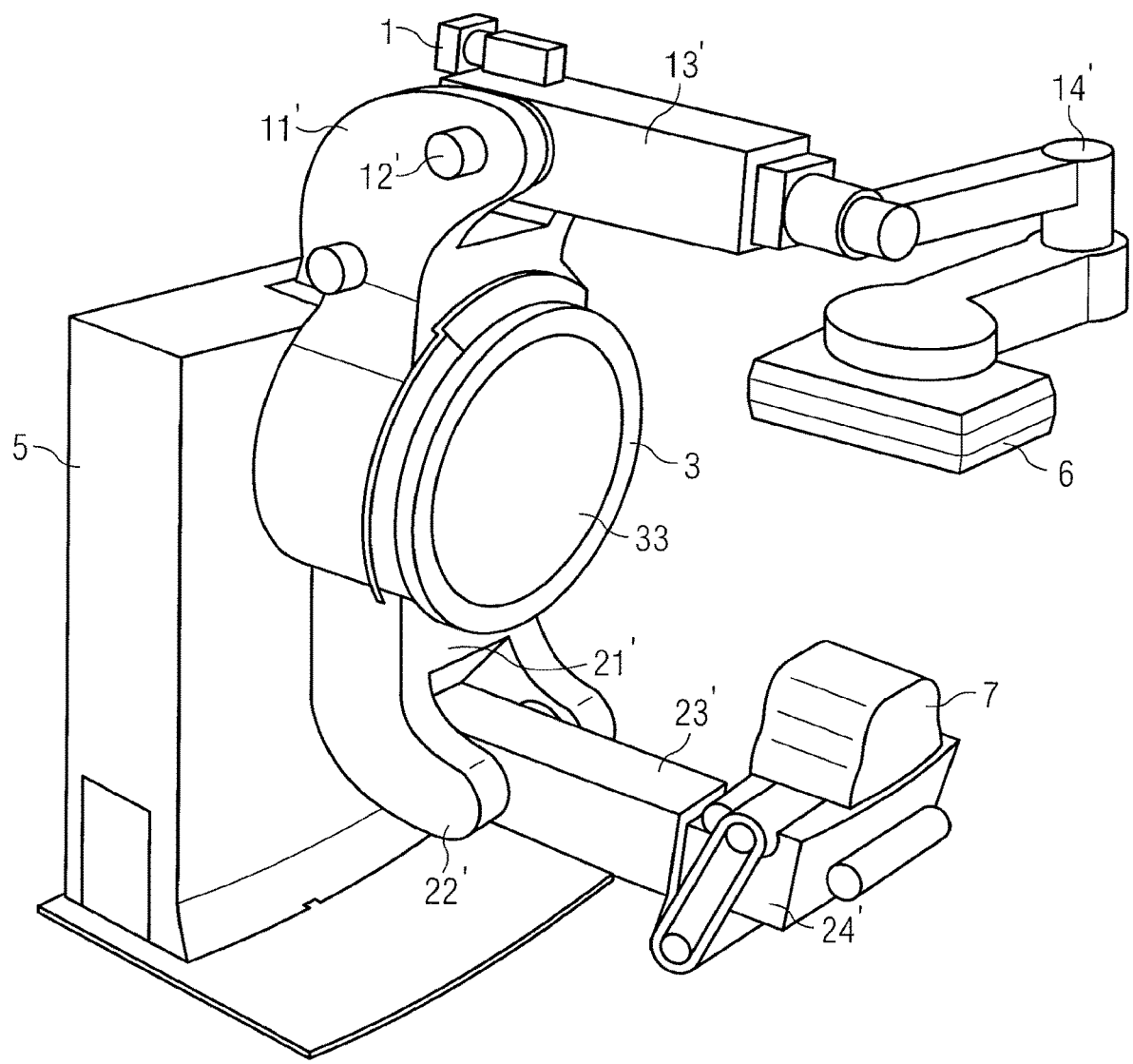
FIG. 4 shows one embodiment of an apparatus for medical examinations.

FIG. 4 shows one embodiment of an apparatus for medical examinations. FIG. 4 shows a first arm 1 formed with the solid body 3, a first arm section 11', a hinge 12' and a second arm section 13'. The first arm 1 also includes a section 14', in which further degrees of freedom are provided. A detector 6 is arranged at an end of the section 14'. Correspondingly, the second arm 2 is formed with a section 21' close to the solid body 3, a hinge 22' and an arm section 23'. The second arm 2 also includes a section 24' that is provided with further degrees of freedom, the function of which is best understood with reference to FIG. 5. The second arm 2 is rotatably fastened to the solid body 3 and carries a radiation source and/or an emitter 7. The solid body 3 provides space in an inner region for the arrangement of components. These components are, for example, a drive controller and/or regulator, a voltage transformer, a water coupling, a data coupling, and/or a power supply coupling. The solid body 3 is closed off using a front wall 33, in order to protect these components from damage. The first arm 1 and/or the solid body 3 rotate relative to a base and/or stand 5, which is configured to be attached to the floor. In one embodiment, the stand 5 is configured as a ceiling stand.

Figure 5:
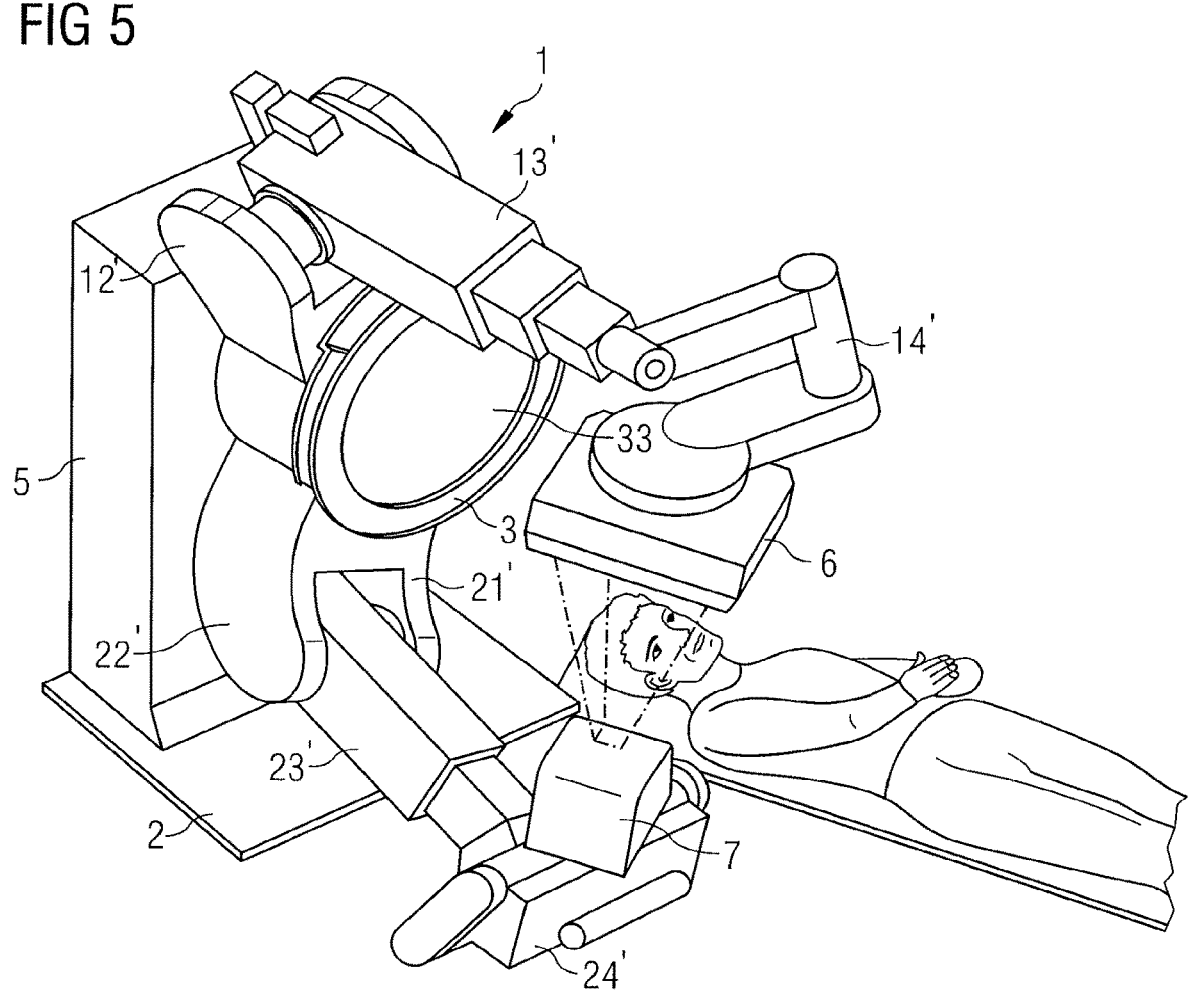
FIG. 5 shows one embodiment of an apparatus for medical examinations in use.

FIG. 5 shows the arrangement from FIG. 4 when used to examine a patient. In the embodiment shown in FIG. 5, the arms 1 and 2 make an angle that differs by 180°, which is predetermined in the same way as the position of the other moveable components by trajectories to be passed through. Further degrees of freedom (e.g. telescopic elements in the arm sections 13' and 23'), and further degrees of freedom in the arm sections 14' and 24' are used such that complex trajectories may be imaged precisely and that the emitter 6 and the detector 7 are positioned in the correct position relative to one another for recordings. The arm 2 may make comparatively small rotational movements in order to realize complex trajectories. This decoupling in rotational (also complete) movements of the arm 1 and (comparatively) minimal relative movements of the arm 2 results in improved design compared to an apparatus for medical examinations with two arms that rotate independently of one another.

The present embodiments are not restricted to those shown in FIGS. 3-5. The present embodiments may be used in each medical field performed using emitters and detectors (e.g., for devices that are specialized with respect to certain examinations, such as mammography devices).

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An apparatus for medical examinations, the apparatus comprising:
    a first arm rotatable about an axis, a first component being disposed on an end of the first arm, the first component being one of a radiation detector and a radiation source;
    a second arm rotatable about the same axis, the second arm carrying a second component on an end of the second arm, the second component being the other of the radiation source and the radiation detector,
    wherein the apparatus further includes, as another end of the first arm, a rotatable solid body, or the other end of the first arm is rigidly secured to a side wall of the rotatable solid body,
    wherein one end of the second arm is movably disposed on the side wall of the rotatable solid body and is positionable along an outer surface of the side wall of the rotatable solid body, such that when the second arm moves along the side wall of the rotatable solid body, the second arm rotates about the axis, relative to the rotatable solid body, the second arm extending away from the outer surface of the side wall to an arm section configured to carry the other of the radiation source and the radiation detector,
    wherein the rotatable solid body is configured to receive a component for high-voltage conversion,
    wherein the rotatable solid body is configured to receive at least one component for transmitting energy, data, or energy and data between a static part of the apparatus and a rotatable part of the apparatus, for furnishing coolant, or a combination thereof, the component for transmitting energy, data, or energy and data comprising at least one slip ring.

2. The apparatus of claim 1, wherein the rotatable solid body for receiving the component for high-voltage conversion is configured to convert a voltage, available in the static part of the apparatus, into a high voltage for the rotatable part of the apparatus.

3. The apparatus of claim 2, wherein the rotatable solid body is configured to perform an endless rotation about the axis during a medical examination.

4. The apparatus of claim 2, wherein the rotatable solid body is drum-shaped, comprises a side wall, comprises a back wall, is closed off by a front wall, or any combination thereof.

5. The apparatus of claim 4, wherein the rotatable solid body is mounted rotatably on a steadying device.

6. The apparatus of claim 5, wherein the first arm, the second arm, or the first arm and the second arm comprise a telescoping portion for translational positioning of the radiation detector, the radiation source, or the radiation detector and the radiation source.

7. The apparatus of claim 6, wherein the first arm is formed by a first portion, including the rotatable solid body and a joint, a telescoping second portion adjoining the first portion, and a further portion, including telescoping spindles, rotational joints, tilting joints, or any combination thereof, adjoining the telescoping second portion.

8. The apparatus of claim 7, wherein the second arm is formed by a portion near the rotatable solid body and including a joint, a telescoping second portion adjoining the portion, and a further portion, including telescoping spindles, rotational joints, tilting joints, or any combination thereof adjoining the telescoping second portion.

9. The apparatus of claim 8, wherein trajectories, predeterminable by the first arm and the second arm, for the radiation source and the radiation detector are transversable.

10. The apparatus of claim 1, wherein the rotatable solid body is configured to perform an endless rotation about the axis during a medical examination.

11. The apparatus of claim 1, wherein the rotatable solid body is drum-shaped, comprises a side wall, comprises a back wall, is closed off by a front wall, or any combination thereof.

12. The apparatus of claim 1, wherein the rotatable solid body is mounted rotatably on a steadying device.

13. The apparatus of claim 1, wherein the first arm, the second arm, or the first arm and the second arm comprise a telescoping portion for translational positioning of the radiation detector, the radiation source, or the radiation detector and the radiation source.

14. The apparatus of claim 1, wherein the first arm is formed by a first portion, including the rotatable solid body and a joint, a telescoping second portion adjoining the first portion, and a further portion, including telescoping spindles, rotational joints, tilting joints, or any combination thereof, adjoining the telescoping second portion.

15. The apparatus of claim 1, wherein the second arm is formed by a portion near the rotatable solid body and including a joint, a telescoping second portion adjoining the portion, and a further portion, including telescoping spindles, rotational joints, tilting joints, or any combination thereof adjoining the telescoping second portion.

16. The apparatus of claim 1, wherein trajectories, predeterminable by the first arm and the second arm, for the radiation source and the radiation detector are transversable.

* * * * *